United States Patent [19]

Suzuki et al.

[11] Patent Number: 4,742,816
[45] Date of Patent: May 10, 1988

[54] OPERATION DEVICE FOR ENDOSCOPES

[75] Inventors: Akira Suzuki; Hiroyuki Sasa, both of Tokyo, Japan

[73] Assignee: Olympus Optical Co., Ltd., Tokyo, Japan

[21] Appl. No.: 43,832

[22] Filed: Apr. 28, 1987

[30] Foreign Application Priority Data

May 2, 1986 [JP] Japan .............................. 61-67230[U]

[51] Int. Cl.[4] ............................................. A61B 1/00
[52] U.S. Cl. ......................................................... 128/4
[58] Field of Search ....................................... 128/4, 6

[56] References Cited

U.S. PATENT DOCUMENTS

| | | | |
|---|---|---|---|
| 4,207,873 | 6/1980 | Kruy | 128/6 |
| 4,461,282 | 7/1984 | Ouchi et al. | 128/4 |
| 4,617,914 | 10/1986 | Ueda | 128/4 |

FOREIGN PATENT DOCUMENTS 60-24672 6/1985 Japan .

Primary Examiner—William H. Grieb
Attorney, Agent, or Firm—Ladas & Parry

[57] ABSTRACT

An operation device for an endoscope is provided including a casing having a through hole and a rotation shaft extending externally from the through hole. The device further includes a first operation unit having a base section located outside the casing such that it is rotatably mounted on the rotation shaft, and an extension section having a finger-operated member at an outer end portion, and a second operation unit having a base section located outside the first operation unit such that it is rotatably mounted on the rotation shaft, and an extension section extending radially from the base section and having an intermediate portion bending toward the casing and a button attached to an outer end. The rotation path of the button is created over the same plane as that of the finger-operated member and spaced apart from that of the finger-operated member at a predetermined angle. A bending operation unit is situated outside the second operation unit and rotatably mounted on the rotation shaft so that a bending tube section of the endoscope may be bent. The operation unit can be readily operated with the same fingers which have gripped the operation body. This assures an improved operability.

5 Claims, 5 Drawing Sheets

F I G. 5
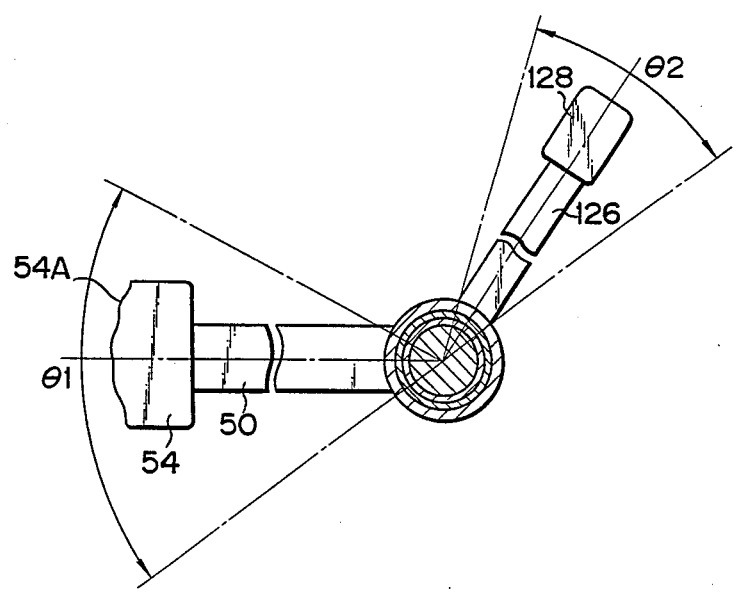

OPERATION DEVICE FOR ENDOSCOPES

BACKGROUND OF THE INVENTION

A. Field of the Invention

This invention relates to an operation device for endoscopes which includes an insertion section containing a bending tube and, in particular, an operation device for endoscopes having a plurality of operation knobs for operating an operation section, such as a bending tube.

B. Description of the Prior Art

An operation section of a typical endoscope contains a bending operation device for bending a bending tube of an insertion section of the endoscope. This type of a bending operation device is disclosed, for example, in Japanese Patent Disclosure (KOKAI) No. 60-246728. In the disclosed bending operation device, a plurality of operation knobs are mounted around a common center axis and respective operation knobs are sequentially mounted one over another on the outer surface of an operation body. The knob for restricting the guiding direction of a treatment instrument inserted through the channel of the endoscope insertion section and the knob for locking a bending operation knob of a bending tube are sequentially mounted on the operation body in which case the bending operation knob is connected to the outside of the restricting knob and locking knob.

The operator has to operate the respective knobs with fingers of the same hand which grips the operation body of the endoscope. The reason is that it is necessary for the operator to use his other hand to move the treatment instrument, which has been inserted through the channel of the endoscope, back and forth. It is also necessary for the operator to perform other operations, with his free hand, such as the operation for inserting the insertion section of the endoscope into a body cavity.

In the conventional operation device of an endoscope, when the operator grips the operation section of the endoscope with his hand, the bending operation knob is located at such a distance from the gripping hand that it is hard for the operator to readily operate the neighboring associated knob with a finger of the same hand.

SUMMARY OF THE INVENTION

It is accordingly the object of this invention to provide an improved operation device for an endoscope which an operator can readily operate the outer-most operation knob of those knobs which are located mutually adjacent each other with one hand.

According to this invention, there is provided an operation device for an endoscope, which comprises:

an operation body including a casing having a through hole and a rotation shaft extending externally from the through hole;

a first operation unit having a base section located outside the casing such that it is rotated on the rotation shaft and an extension section extending radially from the base section and having a finger-operated member at an outer and portion;

a second operation unit having a base section located outside the first operation unit and rotatably mounted on the rotation shaft and an extension section extending radially from the base section and having an intermediate portion bent toward the casing and a button at an outer and portion, in which the rotation path of the button is created over the same plane as that of the finger-operated member and spaced apart from that of the finger-operated member at a predetermined angle; and an operation means located outside the second operation unit such that it is rotatably mounted on the rotation shaft, and adapted to operate a bending tube section of the endoscope.

In the operation device for an endoscope which is manufactured according to this invention, the last-mentioned operation unit can readily be operated by the operator's finger of his gripping hand, thereby assuring an improved operation of the endoscope.

Furthermore, it is possible to solve the problem encountered in a conventional device, where, due to an inadvertent touching of the operation knob by the operator's hand with which the operation body has been gripped, an unintentional lateral force is applied to the operation knob.

Since, according to this invention, the operation device is formed in a compact form, with the center of gravity of the whole operation section shifted toward the operation body, the operation body can readily be gripped and, furthermore, an improved operability can also be attained which is facilitated by the decreased weight of the whole operation section.

BRIEF DESCRIPTION OF THE DRAWINGS

FIG. 5 is a partial view schematically showing a first operation lever and a second operation lever equipped with a button in the embodiment of this invention.

DETAILED DESCRIPTION OF THE PREFERRED EMBODIMENTS

Figure 1:
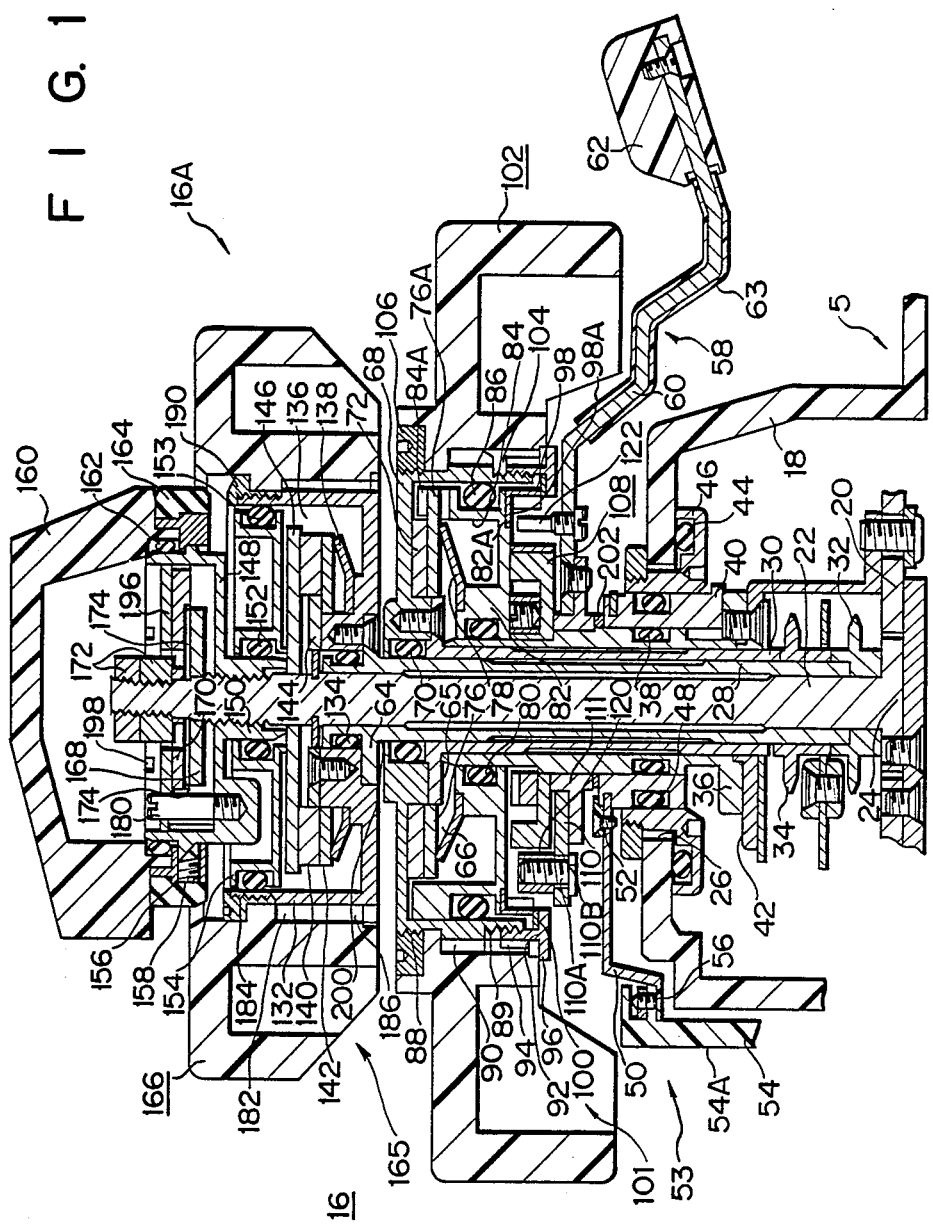
FIG. 1 is a cross-sectional view showing an operation device for an endoscope according to an embodiment of this invention.
Figure 2:
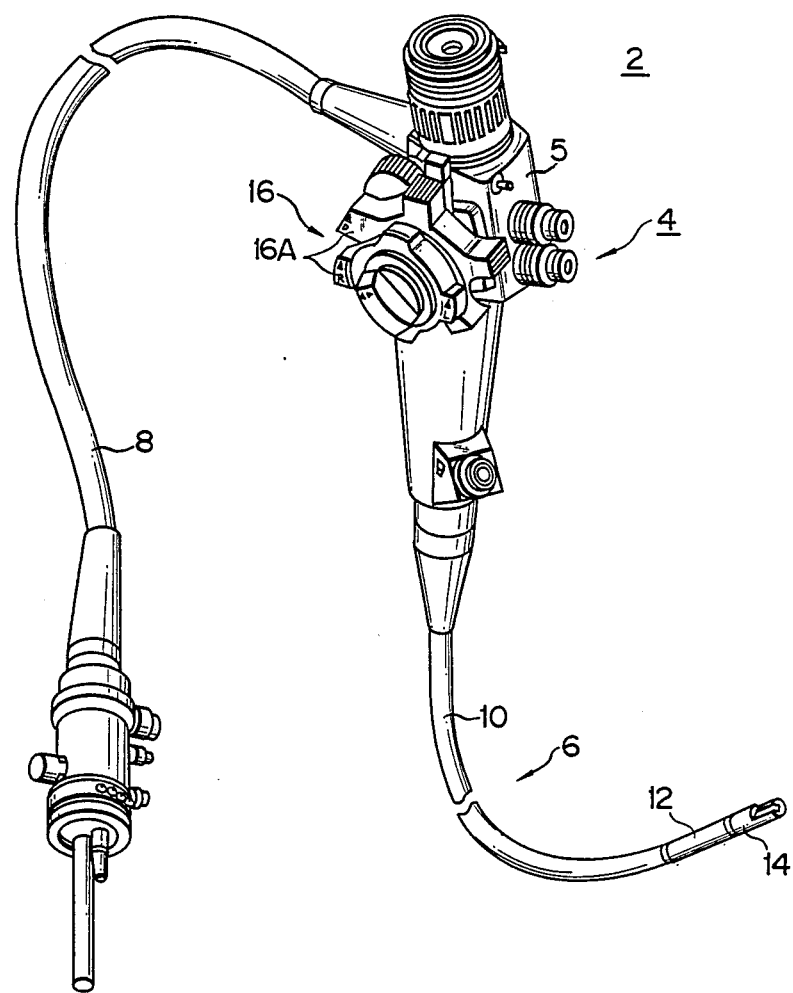
FIG. 2 is a perspective view generally showing an endoscope including the operation device of FIG. 1.

The embodiment of this invention will now be explained below with reference to the accompanying drawings.

FIGS. 1 to 5 disclose one embodiment of this invention. Endoscope 2 shown in FIG. 2 includes operation section 4, insertion section 6 and light guide cable 8. Insertion section 6 includes flexible tube 10 and distal end unit 14 connected through bending tube 12 to the distal end portion of flexible tube 10. Bending operation device 16 is provided at operation section 4 and has bending operation section 16A which extends outwardly from operation section 4. Operation section 16A has first and second bending operation units 101, 165. By operating bending operation section 16A of bending operation device 16, bending tube 12 is remotely operated and bent so that distal end section 14 can be differently bent in the lateral direction as well as in the up and down directions.

Figure 3:
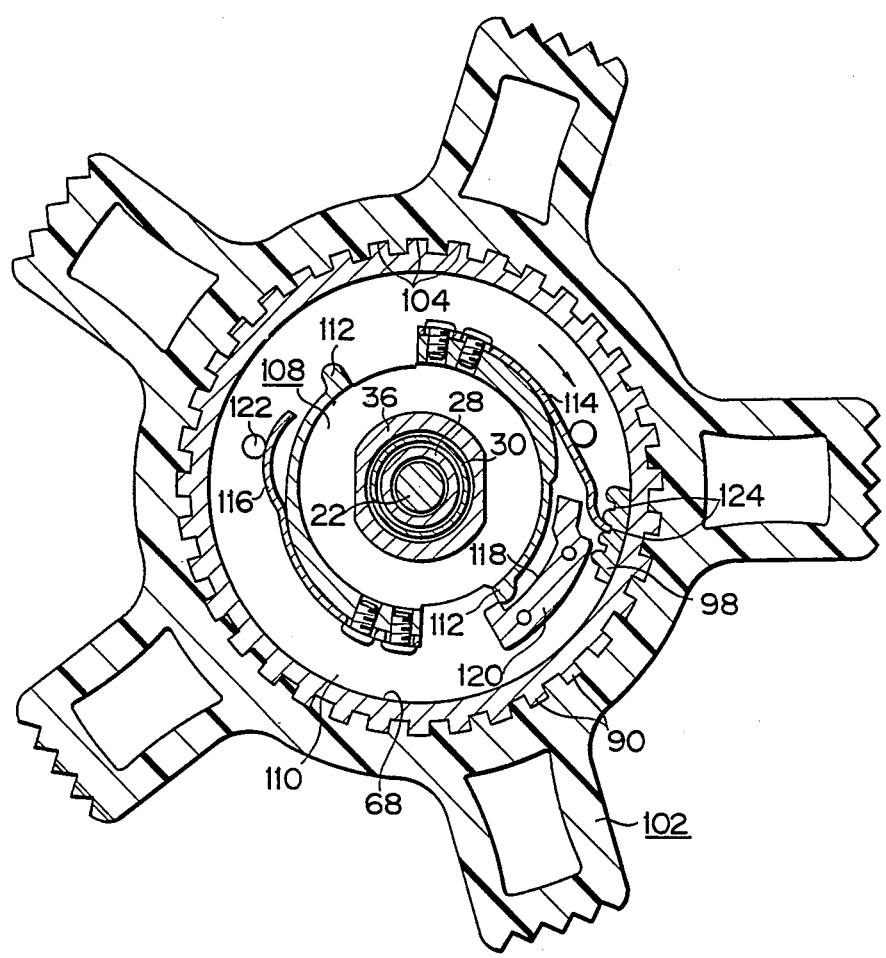
FIG. 3 is a cross-sectional view schematically showing the internal structure of a first bending operation knob in the embodiment of this invention.
Figure 4:
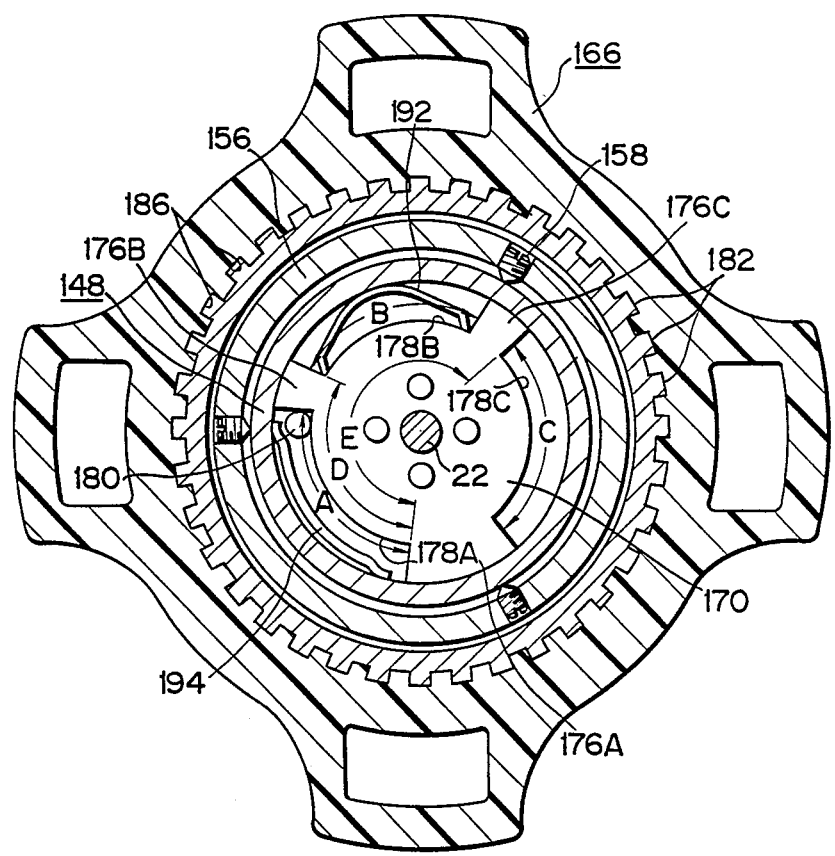
FIG. 4 is a cross-sectional view schematically showing the internal structure of a second bending operation knob in the embodiment of this invention.

Bending operation device 16 is disclosed in FIGS. 1, 3 and 4. In bending operation device 16, casing 18 of operation body 5 is made of an insulating material, such as plastic, and base plate 20 is fixed within casing 18. Shaft 22 is fixed to base plate 20 by flange 24 which is formed at one end of the fixed shaft. The other end of fixed shaft 22 extends outwardly from through hole 26 which is formed in casing 18. First and second sleeves 28 and 30 are rotatably mounted around fixed shaft 22 with the first sleeve arranged around the fixed shaft and the second sleeve arranged around the first sleeve. First sprocket 32 engages with one end of first sleeve 28 such that the first sprocket and sleeve 28 can be rotated as one unit. Second sprocket 34 engages with one end of second sleeve 30 such that the second sprocket and sleeve 28 can be rotated as one unit. A chain means, not shown, having a wire (not shown) coupled to both ends thereof to allow bending tube 12 of insertion section 6 to be bent is in mesh with respective sprockets 32 and 34. Four wires in all are mounted on bending elements, not shown, of bending tube 12 such that they are circumferentially arranged at intervals of 90°. Upon the rotation of first sprocket 32, bending tube 12 is bent in the lateral direction, while, upon the rotation of second sprocket 34, the bending tube is bent in the up-and-down direction.

Fixed cylinder 36 is attached by cover 42 to base plate 20 and second sleeve 30 is rotatably supported inside fixed cylinder 36. Rotation cylinder 40 is mounted outside fixed cylinder 36. Fastening annular member 46 is attached to the edge portion of through hole 26 of casing 18 and rotatable cylinder 40 is rotatably supported by fastening annular member 46. O-rings 38, 48 and 44 are interposed between casing 18 on one side and fixed cylinder 36, rotatable cylinder and fastening annular member 46 on the other side to secure water-proofness within casing 18.

First operation unit 53 includes first operation lever 50 and knob 54. Operation lever 50 for operating a treatment instrument guide element is secured by mounting screw 52 to the outer end of rotation cylinder 40 and extends along the outer surface of casing 18. To the inner end portion of rotation cylinder 40 is fixed a link, not shown, to which the operation wire, not shown, is coupled by a known means. The operation wire is coupled to the treatment instrument guide element, not shown, which is provided within distal end unit 14. Operation knob 54 has finger depression section 54A at the outside thereof and is fixed by screw 56 to the end of first operation lever 50.

Second operation unit 58 is mounted outside first operation unit and has second operation lever 60 bent at its intermediate section toward casing 18 and button 62 as a finger depression section attached to the forward end of operation lever 60 in which case the intermediate section of second operation lever 60 is covered by heat-shrinkable tube 63. The paths of rotation of button 62 and knob 54 are defined in substantially the same plane perpendicular to their rotation axis and their operation ranges $\theta_1$ and $\theta_2$ are located in such a positional relation that the button and knob are not obstructed in their operation as shown in FIG. 5.

First sleeve 28 is formed such that it is longer than second sleeve 30. Sleeves 28 and 30 have flanges 64 and 65, respectively, at their other ends. First support 68 is cap-like in configuration with storage chamber 66 defined therein. First support 68 extends toward casing 18 and is fixed to flange 65 of second sleeve 30 with O-ring 70 inserted between first sleeve 28 and support 68. Within storage chamber 66 of first support 68 are located first and second mounting plates 76 and 82. First mounting plate 76 has friction plate 72 mounted on its upper surface and second mounting plate 82 has leaf spring 78, at the upper surface, bent toward first mounting plate 76 and is rotatably supported with O-ring 80 fitted relative to fixed cylinder 36. Second mounting plate 82 has upwardly extending annular wall 84 as its outer periphery, with O-ring 86 sandwiched between annular wall 84 and the inner wall of first support 68. Cutout 84A is provided in annular wall 84 and projection 76A of first mounting plate 76 engages with cutout 84A. On the outer periphery of first support 68 are sequentially provided first externally threaded section 88, formed along the axis of first support 68, first outer peripheral spline sections 90, each formed at a pitch corresponding to each of 36 circumferentially equally divided sections, and second externally threaded section 89. Annular control member 92 is rotatably threaded on second externally threaded section 89, and second outer peripheral spline sections 94 are formed on the outer periphery of control member 92 such that their pitch corresponds to the pitch of first outer peripheral spline sections 90. Flange 96 is formed at the lower end of control member 92 with one end extending inwardly and the other end extending outwardly. Lower annular member 98 has projection 98A which engages with cutout 82A provided at the lower, outer side edge portion of second mounting plate 82. The inwardly extending portion of flange 96 of control member 92 holds annular member 98 through slide plate 100 made of a material of a smaller frictional coefficient.

When control member 92 is turned, second mounting plate 82 is raised through slide plate 100 and lower annular member 98 so that leaf spring 78 is urged toward first mounting plate 76 with an added force. As a result, friction plate 72 overlying first mounting plate 76 is pressed against first support 68 with added pressure. That is, a frictional force between friction plate 72 and support 68 can freely be selected by turning control member 92.

First operation knob 102 is mounted between first support 68 and control member 92. Knob 102 is made of an electrically insulating material, such as plastic, and has spline sections 104 on the inner wall which correspond to first and second splines 90 and 94. Spline sections 90 and 94 engage with spline section 104. When first operation knob 102 is rotated, first support 68 and control member 92 are rotated as one unit in which case no relative positional displacement occurs between first support 68 and control member 92. That is, after being controlled by control member 92, the aforementioned frictional force can thus be maintained. Press-down ring 106 is threaded on first externally-threaded section 88 of first support 68 to prevent first operation knob 102 from slipping away from the rest of the operation device.

Third mounting plate 108 is provided below second mounting plate 82 such that it cannot be rotated relative to fixed cylinder 36. Fourth mounting plate 110 is mounted below third mounting plate 108 such that it can be freely rotated. Mounting plate 110 has operation lever 60 as already set forth above. A pair of projections 112, 112 are formed on the outer periphery of third mounting plate 108 as shown in FIG. 3, and band-like latching spring 114 and urging spring 116 are fixed at one end to the outer periphery of mounting plate 108. Above fourth mounting plate 110 and outside third mounting plate 108 is provided restricting member 120, which has engaging recess 118. Restricting member 120 is fixed by screw 110A to fourth mounting plate 110, in which case, screw 110A is inserted from below into through hole 110B which is formed at fourth mounting plate 110. Projection 112 engages with engaging recess 118. Fourth mounting plate 110 can be rotated through an angle within which projection 112 abuts against each end of engaging recess 118. Pins 122 are provided such that one is located near the other end of latching spring 114 and one is located near the other end of urging spring 116 above fourth mounting plate 110. Pin 122 has a threaded portion at the base portion and is threaded into the threaded hole of fourth mounting plate 110 with the pin inserted upward from below the fourth mounting plate. When fourth mounting plate 110 is rotated in an arrow-indicated direction from the position of FIG. 3, two pins 122 cause said other ends of said springs 114 and 116 to be elastically deformed toward the axis of fourth mounting plate 110. With fourth mounting plate 110 in the position shown in FIG. 3, said other end of latching spring 114 is latched to one of recesses 124 formed on the inner wall of annular member 98. By so doing, second mounting plate 82 is coupled to third mounting plate 108, thus preventing the rotation of second mounting plate 82. When, in this state, first operation knob 102 is to be rotated, the frictional force between friction plate 72 and first support 68 acts as a rotational resistance of operation knob 102. Operation lever 60, made of metal, is formed integral with mounting plate 110 and thus mounting plate 110 can be operated by operating lever 60.

As shown in FIG. 1, button 62, made of an electric insulating material such as plastic, is attached to the forward end of operation lever 60. The intermediate portion of operation lever 60 is covered by heat-shrinkable tube 63, made of an electric insulating material. Therefore, direct contact with operation lever 60 per se can be avoided.

Second support 132, of a cup-like configuration, is fixed to flange 64 of first sleeve 28 and support 132. Within internal storage chamber 136 of second support 132 are held upwardly bending annular leaf spring 138 and fifth mounting plate 142, with friction plate 140 attached thereto. The leaf spring and fifth mounting plate are movable in the up-and-down direction and are prevented from slipping out of the rest of the operation device by push-down plate 144 which is attached to second support 132. Pressure plate 146 is located on friction plate 140 and freely movable in the up-and-down direction, but never rotatable relative to fixed shaft 22. When push-down member 148 which is threaded on fixed shaft 22 is turned, pressure plate 146 is pushed down by the lower end of boss section 150 of push-down member 148 and pressed against pressure plate 140. That is, a frictional force between pressure plate 146 and friction plate 140 can be controlled by a turning amount of push-down member 148. Sealing member 154 is located between pressure plate 146 and push-down member 148, in which case O-ring 152 is placed to form a seal between the outer periphery of boss section 150 and the inner wall of sealing member 154 and O-ring 153 is placed between the outer periphery of sealing member 154 and second support 132. A plurality of screws 158 are fastened to the outer peripheral wall of push-down member 148 and cup-like operation member 160, covering the upper side of push-down member 148, is attached to annular member 156 in an integral fashion. O-ring 162 is placed between the inner wall of operation member 148 and the outer periphery of push-down member 148. By turning push-down member 148 by operation member 160, it is possible to move pressure plate 146 in the up-and-down direction.

Operation member 160 is integrally formed of an electric insulating material, such as plastic.

Cover ring 164, made of an electric insulating material such as rubber, is fixed to the outer periphery of annular member 156. That is, annular member 156, made of metal, is covered by cover ring 164 of the electric insulating material, in which case the operator never directly touches exposed annular member 156 and thus there is no chance of causing any electric shocks to the operator.

As shown in FIG. 1, since cover ring 164 is mounted on second operation knob 166, inadvertent movement by the operator's finger to a clearance between cover ring 164 and second operation knob 166 rarely occurs, thus positively preventing a possible risk of electric shocks and assuring added safety.

First and second toothed plates 168 and 170 are provided above push-down member 148 with first toothed plate 168 non-rotationally fixed to shaft 22 and second toothed plate 170 rotatable relative to shaft 22. A greater number of teeth 174 are circumferentially mounted at a predetermined pitch such that it is in mesh with first and second toothed plates 168 and 170. As shown in FIG. 4, tongues 176A, 176B and 176C are formed on the outer periphery of second toothed plate 170. First to third restricting grooves 178A, 178B and 178C are formed, by these tongues, as the outer periphery of second toothed plate 170 in a circumferentially spaced-apart relation. The angles A, B and C of respective restricting grooves 178A, 178B and 178C are all set at an equal angle. The relation of the angles D and E showing the relative position among the respective restricting grooves 178A, 178B and 178C are such that the angle D is set to correspond to an integral multiple of the pitch of teeth 174 plus $\frac{1}{3}$ of that pitch and such that the angle E is set to correspond to an integral multiple of the pitch of teeth 174 plus $\frac{2}{3}$ of that pitch. Rotation restricting pin 180 is mounted on the upper surface portion of push-down member 148 such that it extends into one of the restricting grooves, for example, first restricting groove 178A of the angle A, so that push-down member 148 can be rotated within the angle A of first restricting groove 178A. The rotational position of rotation restricting pin 180 can be varied per pitch of teeth 174 by varying the position of the engagement of second toothed plate 170 with first toothed plate 168. That is, a frictional force between pressure plate 146 and friction plate 140 can be controlled for every pitch of teeth 174. With rotation restricting pin 180 set to second restricting groove 178B or third restricting groove 178C, the rotational position of restricting pin 180 can be finely controlled for each $\frac{1}{3}$ of the pitch of teeth 174. From the above it will be appreciated that, in the embodiment, the turning amount of push-down member 148 can be controlled in three stages, or in three incremented stages, in combination with the number of teeth 174.

Viewed from the bottom-up direction, outer peripheral spline sections 182 and externally-threaded section 184 are sequentially formed on the outer periphery of second support 132. Second operation knob 166 has spline sections 182 on its inner wall and is mounted on spline sections 182 of support 132, in which case second operation knob 166 is prevented from slipping away from the rest of hold-down ring 190. If, therefore, second support 132 is rotated by second operation knob 166, first sleeve 28 is operated in interlock with the rotation of support 132, causing bending tube 12 of insertion section 6 to be bent in the lateral direction. Since, at this time, a frictional force between friction plate 140 and pressure plate 146 acts as a rotational resistance, second operation knob 166 is either made stationary or can be finely controlled in that rotation angle. The frictional force between friction plate 140 and pressure plate 146 can be controlled by operation member 160.

Hold-down ring 190 may be formed of an electric insulating material, but is preferably formed of metal so as to achieve added strength. As shown in FIG. 1, hold-down ring 190 is located at a somewhat lower level down from the upper end of the inner wall of operation knob 166, with the hold-down ring covered by operation knob 166, made of an electric insulating material. Thus, there is no risk that direct contact of the operator's finger to hold-down ring 190 will occur or that the operator will encounter electric shocks from that direct contact.

Positioning spring 192 and click spring 194 are provided on the upper surface of push-down member 148 as shown in FIG. 4, the positioning spring preventing an undesirable displacement between first toothed plate 168 and second toothed plate 170 and the click spring, when push-down member 148 is rotated through a predetermined range, elastically engaging with rotation restricting pin 180 at the termination of the rotation. Plate 196 for preventing positioning spring 192 and click spring 194 from slipping off the associated member is attached to toothed plate 170 and toothed plates 168 and 170 and plate 196 are prevented from being clattered in the up-and-down direction by boss section 198 which is projected from the lower surface of operation member 160.

In bending operation device 16 thus constructed, if first support 68 and associated control member 92 are rotated relative to each other in the step of assembling first operation knob 102, then it is possible to control the strength with which leaf spring 78 urges toward first mounting plate 76. It is, therefore, possible to vary the frictional force acting between first support 68 and friction plate 72 attached to first mounting plate. The rotational resistance of operation knob 102 can be controlled simply by turning first support 68 and control member 92 relative to each other. After the rotational resistance of operation knob 102 has been controlled, first spline sections 90 of first support 68 and second spline sections 94 of control member 92 are arranged in a series array and first operation knob 102 is mounted while spline sections 104 are brought into meshing engagement with spline sections 90 and 94. By the meshing engagement of spline sections 90 and 94 with spline section 104, first support 68 and control member 92 are prevented from being rotated relative to each other, thus maintaining the rotational resistance of operation knob 102 constant.

The aforementioned rotational resistance can be controlled by relatively rotating first support 68 and control member 92 in units of one pitch of respective spline sections 90 and 94. Since, in the embodiment, spline sections 90 and 94 are each formed at a pitch corresponding to each of 36 equal division portions, it is possible to make a very fine control. This structure allows the rotational torque of first operation knob 102 to be distributed among the respective spline sections 104 and there is no risk that, as in the conventional construction where operation knob 102 is coupled by, for example, one knock pin to support 68, stress will be concentrated on the one knock pin.

In operation section 16A of bending operation unit 16, the operator can manually operate first operation member 53, second operation member 58, first operation knob 102, second operation knob 166 and operation member 160, noting that some of these members are made of electric insulating material and the others are covered with the insulating material, that is, all of these metal members are covered with electric insulating material. There is no possibility that, when a high-frequency treatment instrument is used within the channel of the endoscope, the operator will encounter electric shocks due to the flow of high-frequency leakage current through these members when directly touched by his fingers.

In this embodiment, button 62 of operation member 58 is brought down to the level at which the other operation knob 54 is situated. The levels of first and second operation knobs 102, 116, and operation member 160 can sequentially be lowered. Where the respective operation members are to be operated with the operator's fingers with which operation section 4 of the endoscope has been gripped, it is easier for the operator to manually operate operation members since they are situated in the neighborhood of the gripping hand, thus assuring an improved operability.

This invention is not restricted to the aforementioned embodiment. For example, first operation member 53 of the first embodiment may be used for controlling the focus of an objective optical system of the endoscope. In this case, a focal control wire is connected through a link to the inner end of rotatable cylinder 40 and focal control is performed by pushing and pulling the focal control wire.

In a modified form of the operation device, a focal control knob and treatment instrument raising means may be located in a common plane perpendicular to the rotation shaft.

This invention can equally be applied to any operation device for the operation section of an endoscope.

What is claimed is:

1. An operation device for an endoscope which includes a plurality of operation sections having first and second operation sections, said operation device comprising:
    an operation body including a casing having a through hole and a rotation shaft externally extending through said through hole;
    a first operation unit for operating said first operation section, said first operation unit having a base section located outside said casing such that it is rotatably mounted on said rotation shaft, and an extension section extending radially from said base section and having a finger-operated member at an outer end portion;
    a second operation unit having a base section located outside said first operation unit such that it is rotatably mounted on said rotation shaft, and an extension section extending radially from said basic section and having an intermediate portion bent toward said casing and a button attached to an outer end portion, said rotation path of said button being created over the same plane as that of said finger-operated member such that it is spaced apart from the rotation path of said finger-operated member at a predetermined angle; and operation means located outside said second operation unit such that it is rotatably mounted on said rotation shaft, said operation means operating the other associated operation sections.

2. The operation device according to claim 1, wherein said casing, said finger-operated member of said first operation unit, said button of said second operation unit, and externally exposed portions of said operation means are formed of an electric insulating material.

3. The operation device according to claim 1, wherein said operation means has first and second bending operation units for bending an insertion section of the endoscope, said first and second bending operation units being adapted to control rotational resistance.

4. The operation device according to claim 3, wherein said second operation unit has fixing means for fixing said first bending unit.

5. The operation device according to claim 1, wherein said operation means has a bending operation unit for bending an insertion section of the endoscope, said bending operation unit having an operation knob extending over the intermediate portion of said second operation unit.

* * * * *